United States Patent [19]

Garabedian

[11] Patent Number: Plant 5,902

[45] Date of Patent: Mar. 17, 1987

[54] PLUM TREE, RANCH 9 MAROON

[76] Inventor: John M. Garabedian, 3104 E. Huntington Blvd., Fresno, Calif. 93702

[21] Appl. No.: 766,444

[22] Filed: Aug. 19, 1985

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A plum tree broadly characterized by producing fruit which has a Deep Maroon color, heavy Blue-Gray blush, and a firm flesh which is a Deep Red in color throughout and a semi-freestone whose surfaces are stained Red from the flesh pigments.

1 Drawing Figure

BACKGROUND OF THE NEW VARIETY

The present invention relates to a new and distinct variety of plum tree which has been denominated by the varietal name "Ranch 9 Maroon" and which is remotely similar to the Roysum Plum (U.S. Plant Pat. No. 2,619), which matures at approximately the same time, but is distinguished therefrom by having a darker, more full colored Maroon skin color which possesses a heavy Blue-Gray bloom, and a flesh portion that presents a full Red "blood" appearance.

It has long been known that the purchase of fruits, such as plums by consumers, is often largely influenced by the fruit size and exterior coloration. Thus it has been recognized that it is desirable to provide a plum tree bearing fruit having the commercially aesthetic appeal of fruit such as that presented by the present invention, which can be brought to market to compete with fruits being marketed, such as the Roysum Plum that are being harvested in the same season. The fruit of the subject variety has stones that are characterized by being stained red from the flesh pigments which are in close proximity therewith.

ORIGIN AND ASEXUAL REPRODUCTION OF THE NEW VARIETY

For many years, the applicant has sought to produce improved varieties of plum trees by cross pollinating selected trees which have desirable characteristics. Pursuant to such an objective, a seedling of unknown origin was grown by me in 1977 at the John M. Garabedian Farm located at Kings Canyon Road and Fowler Avenue, in the City of Fresno, County of Fresno, and State of California. Upon discovering that this particular seedling had characteristics that were desired by me, the seedling was then budded to stock trees in 1980 which were planted on Ranch No. 9, which is located on the corner of Fowler and Belmont Avenue in the City of Fresno, County of Fresno, and State of California. The budded plum trees planted at Ranch No. 9 have been continuously observed by me, and have proved to be identical in characteristics to those displayed by the original seedling.

SUMMARY OF THE NEW VARIETY

The instant variety of plum tree is characterized by a fruit which ripens late in the season, approximately the first of September. The fruit has a firm meat with a mild, delicate taste and exhibits excellent storage qualities.

The new plum tree bears fruit which skin color attains a dark, full-colored Maroon (MCC 47-16) and has a Blood Red-colored flesh (MCC 37-13) with a few, fine and tender fibers.

DETAILED DESCRIPTION

Referring more particularly to the pomological details of the new and distinct variety of plum tree, the following has been observed under the ecological conditions prevailing in the designated orchard in Fresno County, Calif. All color code identifications are made by reference to the Munsell Limit Color Cascade. Common descriptive color names are also used.

The drawing shows fruit and foliage of the new variety.

TREE

Figure: Upright, spreading, open and vase formed.
Size: Medium.
Productivity: Productive.
Regularity of bearing: Regular.
Vigor: Medium in vigor.
Trunk:
- *Diameter in relation to length.*—Medium.
- *Surface characteristics.*—Medium surface texture.

Branches:
- *Size.*—Medium in diameter.
- *Surface texture.*—Medium.
- *Color.*—Dull Gray.

Lenticels:
- *Number.*—Medium.
- *Size.*—Small.

LEAVES

Shoot:
- *Size.*—Medium.
- *Shape.*—Slightly obovate, acuminate, acutely pointed.
- *Length.*—11.64±0.09 cm.
- *Width.*—4.58±0.27 cm.
- *Thickness.*—Medium.
- *Color.*—Ventral surface — Medium Green (MCC 22-13 to 21-14).
- *Marginal form.*—Crenate.
- *Leaf texture.*—Nearly smooth.
- *Petiole.*—Short to medium; average length — 1.18±0.12 cm.; thickness — medium.

*Glands.*—Variable in number, from 1 to 4; positioned generally opposite to each other; Size — small; Shape — mixed; Color — Green; Location — at the base of the blade and/or on the petiole.

*Stipules.*—Linear and ephemeral.

Spur:

*Size.*—Small.

*Shape.*—Narrow obovate, acuminate, pointed; base — long acuminate.

*Length.*—8.92±1.01 cm.

*Width.*—3.01±0.24 cm.

*Color.*—Medium Green (MCC 22-3 to 21-14).

*Leaf texture.*—Nearly smooth.

*Thickness.*—Medium.

*Marginal form.*—Crenate.

*Petiole.*—Short; 1.19±0.26 cm.

*Color.*—Medium Green (MCC 22-13 through 21-14).

*Glands.*—Completely lacking.

Flower buds:

*Size.*—Small.

*Shape.*—Glabrous, plump.

*Position.*—Appressed; obtuse.

*Color.*—Medium Brown.

Flowers:

*Date of first bloom.*—Feb. 28, 1984.

*Date of full bloom.*—Mar. 5, 1984.

*Color.*—White.

*Size.*—Medium.

*Date of bloom.*—Average as compared with other varieties.

FRUIT

Maturity when described: Ripe for eating, September 8.

Size: Uniform, medium to large.

*Diameter transverse in cheek plane.*—5.97±0.32 cm.

*Diameter transverse in suture plane.*—5.86±0.32 cm.

*Axial diameter.*—5.30±0.32 cm.

Form: Uniform; usually somewhat oblate, occasionally broad ovate; very slightly unsymmetrical with the apex ventral to the stem.

Suture: An inconspicuous shallow groove extending from the base to the apex; there is a slight to marked depression at the pistil point.

Bloom:

*Color.*—Blue-Gray (MCC 2-4).

*Amount.*—Heavy.

Dots: Numerous in number, small, round, Medium Brown, numerous on the cheeks and dorsal side, more numerous apically; lacking along ventral suture, shoulders and the cavity.

Ventral surface: Rounded slightly, lipped towards the base and apex with the lips being nearly equal.

Stem cavity: Rounded, circular to very slightly elongated in the suture plane, with suture showing on one side.

*Width.*—2.40±0.14 cm.

*Depth.*—1.14±0.11 cm.

*Markings.*—None observable.

*Base.*—Broadly rounded, to occasionally truncate.

*Apex.*—Occasionally rounded, usually truncated; often depressed.

*Pistil point.*—Apical.

Stem:

*Length.*—Short, and stout.

Skin:

*Thickness.*—Thick.

*Texture.*—Medium; tenacious to flesh; somewhat bitter.

*Tendency to crack.*—no observed tendency to crack in the dry season.

*Down.*—Wanting.

*Ground color.*—Light Amber (MCC 32-4 to 32-5).

*Skin color.*—Dark Maroon Red (MCC 47-16).

Flesh:

*Flesh color.*—Diffused Medium Deep Red throughout (MCC 37-13).

*Pit cavity.*—Color slightly darker than flesh.

*Texture.*—Firm, fine and meaty.

*Amygdalin.*—Wanting.

*Juice.*—Moderate to scant; rich.

*Fibers.*—Few, fine and tender.

*Ripening.*—Even.

*Flavor.*—Sweet, mild and delicate.

*Aroma.*—Wanting.

*Eating quality.*—Good.

Stone: Semi-freestone, adheres to the flesh along both the dorsal and ventral edges of the stone.

*Size.*—Small to medium.

*Length.*—2.18±0.11 cm.

*Breadth.*—1.89±0.11 cm.

*Thickness.*—1.19±0.08 cm.

*Form.*—Broad oval.

*Base.*—Straight.

*Hilum.*—Narrow, oval.

*Apex.*—Rounded to the tip.

*Sides.*—Nearly equal.

*Surface.*—Rather finely roughened, often lightly ridged basally; dorsal edge is longer, often being recurved basally.

*Ventral edge.*—Medium, usually without wing.

*Dorsal edge.*—Narrow, with an additional narrow groove toward the base.

*Ridges.*—Interrupted.

*Color.*—Cheek surfaces of stone are stained Red (MCC 42-14); sutures of stone are a Light Brown (MCC 31-3 to 33-4).

*Tendency to split.*—Slight.

Use: Market and dessert.

Keeping quality: Good.

Resistance to insects: Medium.

Resistance to disease: Medium.

Shipping quality: Good.

Although the new variety of plum tree possesses the desired characteristics under the growing conditions prevailing in Fresno County, Calif., in the central portion of the San Joaquin Valley, it is to be understood that variations of the usual magnitude in characteristics incident to changes in growing conditions, fertilization, pruning and pest control are to be expected.

Having described my new variety of plum tree, what I claim as new is:

1. A new and distinct variety of plum tree substantially as illustrated and described, broadly characterized by its maturity date which is approximately the same as the Roysum Plum (U.S. Plant Pat. No. 2,619) which it is most similar to, but which it is distinguished therefrom as to novelty by its fruit having a skin of a color of Dark Maroon with a heavy Blue-Gray bloom, whose flesh is Medium to Deep Red throughout and by a stone whose cheek surfaces are stained Red from the flesh pigments.

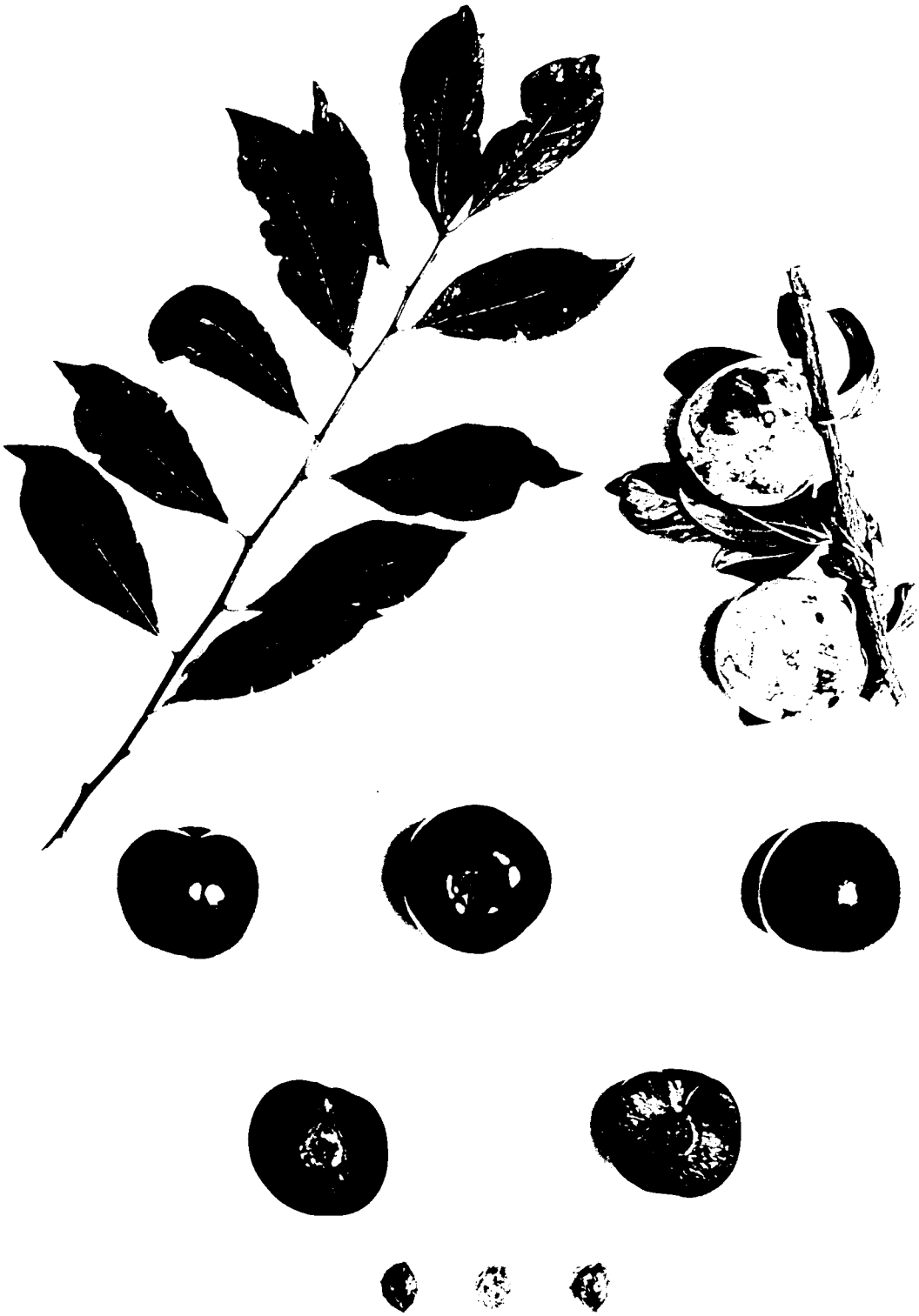

* * * * *